United States Patent [19]
Hyatt et al.

[11] Patent Number: 5,730,721
[45] Date of Patent: Mar. 24, 1998

[54] MEDICAL APPLICATOR AND METHOD

[75] Inventors: Gary F. Hyatt, Randleman; William M. Bostic, Asheboro, both of N.C.

[73] Assignee: Vesture Corporation, Asheboro, N.C.

[21] Appl. No.: 591,726

[22] Filed: Jan. 25, 1996

[51] Int. Cl.$^6$ .................................................. A61M 31/00
[52] U.S. Cl. ........................... 604/49; 604/113; 128/898; 607/108
[58] Field of Search .............................. 604/20, 49, 19, 604/113, 114, 246, 890.1; 128/898; 602/45, 58; 607/108, 115; 424/427, 449

[56] References Cited

U.S. PATENT DOCUMENTS

| | | |
|---|---|---|
| Re. 34,089 | 10/1992 | Kydonieus et al. . |
| Re. 34,692 | 8/1994 | Becher . |
| 4,078,568 | 3/1978 | Etes et al. . |
| 4,307,717 | 12/1981 | Hymes et al. . |
| 4,379,454 | 4/1983 | Campbell et al. . |
| 4,402,696 | 9/1983 | Gulko . |
| 4,486,193 | 12/1984 | Shaw et al. . |
| 4,486,194 | 12/1984 | Ferrara . |
| 4,568,343 | 2/1986 | Leeper et al. . |
| 4,573,995 | 3/1986 | Chen . |
| 4,573,996 | 3/1986 | Kwiatek et al. . |
| 4,588,400 | 5/1986 | Ring et al. . |
| 4,588,580 | 5/1986 | Gale et al. . |
| 4,597,961 | 7/1986 | Etscorn . |
| 4,601,893 | 7/1986 | Cardinal . |
| 4,615,699 | 10/1986 | Gale et al. . |
| 4,624,665 | 11/1986 | Nuwayser . |
| 4,627,429 | 12/1986 | Tsuk . |
| 4,638,043 | 1/1987 | Szycher et al. . |
| 4,645,502 | 2/1987 | Gale et al. . |
| 4,650,484 | 3/1987 | Shaw et al. . |
| 4,655,767 | 4/1987 | Woodard . |
| 4,655,768 | 4/1987 | Marecki et al. . |
| 4,661,105 | 4/1987 | Gale . |
| 4,666,441 | 5/1987 | Andriola et al. . |
| 4,671,267 | 6/1987 | Stout . |
| 4,681,584 | 7/1987 | Gale et al. . |
| 4,685,911 | 8/1987 | Konno et al. . |
| 4,687,481 | 8/1987 | Nuwayser . |
| 4,693,711 | 9/1987 | Bremer et al. . |
| 4,695,277 | 9/1987 | Lauk . |
| 4,704,119 | 11/1987 | Shaw et al. . |
| 4,708,716 | 11/1987 | Sibalis . |
| 4,710,191 | 12/1987 | Kwiatek et al. . |
| 4,725,272 | 2/1988 | Gale . |
| 4,743,249 | 5/1988 | Loveland . |
| 4,743,499 | 5/1988 | Volke . |
| 4,746,515 | 5/1988 | Cheng et al. . |
| 4,747,841 | 5/1988 | Kuratomi . |
| 4,747,845 | 5/1988 | Korol . |
| 4,758,434 | 7/1988 | Kydonieus et al. . |
| 4,762,124 | 8/1988 | Kerch . |
| 4,765,478 | 8/1988 | Bringloe . |
| 4,777,346 | 10/1988 | Swanton, Jr. . |
| 4,784,857 | 11/1988 | Berry et al. . |
| 4,788,064 | 11/1988 | Patel . |
| 4,797,284 | 1/1989 | Loper . |
| 4,821,740 | 4/1989 | Tachibana . |
| 4,822,617 | 4/1989 | Panoz . |
| 4,830,855 | 5/1989 | Stewart . |
| 4,830,856 | 5/1989 | Peppers . |
| 4,834,978 | 5/1989 | Nuwayser . |
| 4,834,979 | 5/1989 | Gale . |

(List continued on next page.)

*Primary Examiner*—Michael Powell Buiz
*Assistant Examiner*—Bhisma Mehta
*Attorney, Agent, or Firm*—Merchant, Gould, Smith, Edell, Welter & Schmidt, P.A.

[57] ABSTRACT

A medical applicator and method of use includes in one embodiment, a flexible envelope containing medicinal fluid which is delivered to the patient via apertures in the envelope. The envelope is formed from a flexible plastic material which can be heated in a microwave, electrical resistance or other ovens. Other embodiments may allow refrigeration of the medicinal fluids. A carrier envelope is provided in another embodiment to maintain the medicinal fluid at a desired temperature for prolonged periods of time. The medicinal fluids may be topical or may be formulated for transdermal treatment of the patient for analgesic purposes, antibiotic delivery or otherwise as desired.

11 Claims, 3 Drawing Sheets

U.S. PATENT DOCUMENTS

| | | |
|---|---|---|
| 4,844,903 | 7/1989 | Seth . |
| 4,849,224 | 7/1989 | Chang . |
| 4,857,334 | 8/1989 | Korol . |
| 4,863,738 | 9/1989 | Taskovich . |
| 4,868,898 | 9/1989 | Seto . |
| 4,877,618 | 10/1989 | Reed, Jr. . |
| 4,879,119 | 11/1989 | Konno et al. . |
| 4,880,416 | 11/1989 | Horiuchi et al. . |
| 4,880,633 | 11/1989 | Loper et al. . |
| 4,898,592 | 2/1990 | Latzke . |
| 4,900,555 | 2/1990 | Cheng . |
| 4,904,475 | 2/1990 | Gale et al. . |
| 4,908,027 | 3/1990 | Enscore et al. . |
| 4,908,213 | 3/1990 | Govil et al. . |
| 4,910,020 | 3/1990 | Samour . |
| 4,911,707 | 3/1990 | Heiber et al. . |
| 4,913,905 | 4/1990 | Fankhauser et al. . |
| 4,913,957 | 4/1990 | Strack et al. . |
| 4,915,950 | 4/1990 | Miranda et al. . |
| 4,917,676 | 4/1990 | Heiber et al. . |
| 4,917,688 | 4/1990 | Nelson . |
| 4,917,895 | 4/1990 | Lee et al. . |
| 4,933,184 | 6/1990 | Tsuk . |
| 4,940,456 | 7/1990 | Sibalis . |
| 4,940,586 | 7/1990 | Cheng et al. . |
| 4,942,037 | 7/1990 | Bondi et al. . |
| 4,942,883 | 7/1990 | Newman . |
| 4,956,171 | 9/1990 | Chang . |
| 4,983,395 | 1/1991 | Chang et al. . |
| 4,990,340 | 2/1991 | Hidaka et al. . |
| 4,997,656 | 3/1991 | Shikinami et al. . |
| 5,004,610 | 4/1991 | Osborne . |
| 5,013,545 | 5/1991 | Blackman et al. . |
| 5,024,838 | 6/1991 | Parrilla . |
| 5,028,431 | 7/1991 | Franz et al. . |
| 5,035,894 | 7/1991 | Lee et al. . |
| 5,040,677 | 8/1991 | Tubo et al. . |
| 5,045,601 | 9/1991 | Capelli et al. . |
| 5,047,244 | 9/1991 | Sanvordeker et al. . |
| 5,049,387 | 9/1991 | Amkraut . |
| 5,050,595 | 9/1991 | Krafft . |
| 5,064,422 | 11/1991 | Wick . |
| 5,066,494 | 11/1991 | Becher . |
| 5,071,656 | 12/1991 | Lee et al. . |
| 5,079,008 | 1/1992 | Sinnreich et al. . |
| 5,122,382 | 6/1992 | Gale et al. . |
| 5,124,157 | 6/1992 | Colley et al. . |
| 5,128,124 | 7/1992 | Fankhauser et al. . |
| 5,132,115 | 7/1992 | Wolter et al. . |
| 5,141,750 | 8/1992 | Lee et al. . |
| 5,150,707 | 9/1992 | Anderson . |
| 5,156,847 | 10/1992 | Lewis et al. . |
| 5,171,576 | 12/1992 | Amkraut et al. . |
| 5,196,202 | 3/1993 | Konishi . |
| 5,215,751 | 6/1993 | Müller . |
| 5,217,718 | 6/1993 | Colley et al. . |
| 5,223,261 | 6/1993 | Nelson et al. . |
| 5,230,897 | 7/1993 | Griffin et al. . |
| 5,234,690 | 8/1993 | Chiang et al. . |
| 5,242,433 | 9/1993 | Smith et al. . |
| 5,244,677 | 9/1993 | Kreckel et al. . |
| 5,252,334 | 10/1993 | Chiang et al. . |
| 5,254,109 | 10/1993 | Smith et al. . |
| 5,254,346 | 10/1993 | Tucker et al. . |
| 5,268,209 | 12/1993 | Hunt et al. . |
| 5,271,940 | 12/1993 | Cleary et al. . |
| 5,273,755 | 12/1993 | Venktrama et al. . |
| 5,273,756 | 12/1993 | Fallon et al. . |
| 5,273,757 | 12/1993 | Jaeger et al. . |
| 5,277,180 | 1/1994 | Angelillo et al. . |
| 5,284,660 | 2/1994 | Lee et al. . |
| 5,296,222 | 3/1994 | Petersen et al. . |
| 5,300,105 | 4/1994 | Owens . |
| 5,304,379 | 4/1994 | Cormier et al. . |
| 5,306,502 | 4/1994 | Jaeger et al. . |
| 5,330,452 | 7/1994 | Zook . |
| 5,336,213 | 8/1994 | D'Angelo et al. . |
| 5,336,255 | 8/1994 | Kanare et al. . |
| 5,342,623 | 8/1994 | Enscore et al. . |
| 5,344,656 | 9/1994 | Enscore et al. . |
| 5,350,581 | 9/1994 | Kochinke . |
| 5,352,456 | 10/1994 | Fallon et al. . |
| 5,352,457 | 10/1994 | Jenkins . |
| 5,356,632 | 10/1994 | Gross et al. . |
| 5,364,628 | 11/1994 | Kissel et al. . |
| 5,364,630 | 11/1994 | Osborne et al. . |
| 5,368,581 | 11/1994 | Smith et al. . |
| 5,405,671 | 4/1995 | Kamin et al. . |
| 5,411,739 | 5/1995 | Jaeger et al. . |
| 5,411,740 | 5/1995 | Lee et al. . |
| 5,415,866 | 5/1995 | Zooki . |
| 5,417,674 | 5/1995 | Smith et al. . |
| 5,438,067 | 8/1995 | Jalonen et al. . |
| 5,451,407 | 9/1995 | Cormier et al. . |
| 5,460,620 | 10/1995 | Smith et al. . |
| 5,462,744 | 10/1995 | Gupte et al. . |
| 5,462,745 | 10/1995 | Enscore et al. . |
| 5,462,746 | 10/1995 | Wolter et al. . |
| 5,466,465 | 11/1995 | Royds et al. . |
| 5,466,466 | 11/1995 | Müller . |
| 5,468,501 | 11/1995 | Kydonieus . |
| 5,470,323 | 11/1995 | Smith et al. . |
| 5,474,783 | 12/1995 | Miranda . |
| 5,484,603 | 1/1996 | Holden et al. . |
| 5,487,889 | 1/1996 | Eckert et al. . |
| 5,487,932 | 1/1996 | Dunshee . |
| 5,494,680 | 2/1996 | Peterson . |
| 5,500,222 | 3/1996 | Lee et al. . |
| 5,503,843 | 4/1996 | Santus et al. . |
| 5,503,844 | 4/1996 | Kwiatek et al. . |
| 5,505,957 | 4/1996 | D'Angelo et al. . |
| 5,505,958 | 4/1996 | Bello et al. . |
| 5,508,039 | 4/1996 | Yates et al. . |
| 5,512,292 | 4/1996 | Gale et al. . |
| 5,630,961 | 5/1997 | Salee . |

5,730,721

MEDICAL APPLICATOR AND METHOD

FIELD OF THE INVENTION

The invention herein pertains to a device for heating or cooling body tissues and/or medicinal fluids during application of medicinal fluids to body tissues.

BACKGROUND AND OBJECTIVES OF THE INVENTION

It is sometimes important to control the tissue temperature and/or medicine temperature during administration of certain medications such as topical applications of various antiseptic solutions or analgesics, as the relief effectiveness afforded may be related to duration and temperature of the application. Additionally, transdermal absorption of various antibodies can be regulated through heating of the skin and subcutaneous tissues which provides the patient improved therapy. With acute injuries, reduced blood flow from ruptured vesicular damage is benefited by cold application. Certain heated analgesic solutions offer enhanced relief for muscle aches and pains. However, it has been difficult in the past to regulate the temperature of a particular body area or to supply warmed or cooled medications to an area of the body without undesired effort in maintaining the specific body area and medication at a uniform design temperature. Reheating or recooling of medications is difficult and time-consuming, oftentimes requiring a nurse or technician to expend substantial efforts to supervise and assist. Keeping a body area sufficiently warmed or cooled likewise is difficult, requiring expensive equipment in certain instances.

Thus, with the problems and inconveniences of conventional medical application devices and methods, the present invention was conceived and one of its objectives is to provide a medical applicator for delivery of temperature controlled medicines in an easy and simple manner.

It is another objective of the present invention to provide a medical applicator and method in which the applicator can be heated or refrigerated and from which a temperature varied medicinal fluid contained therein can be applied to the patient. Herein the term "temperature varied" refers to variance in temperature from the ambient temperature, typically room temperature.

Still another objective of the present invention is to provide, in one preferred embodiment, a medical applicator having a first carrier envelope for use as a body tissue temperature controller and a second envelope attached thereto containing the temperature controlled medication for release onto the patient.

It is another objective of the present invention to provide a method of applying temperature controlled medicine through an egress such as apertures defined in a flexible envelope.

A further objective of the invention is to provide a medical applicator which will allow the delivery of transdermal anticoagulants or localized anaesthesia to reduce swelling as well as clot formation, in conjunction with the pain relief.

Various other objectives and advantages of the invention will become apparent to those skilled in the art as a more detailed understanding of the invention is realized by the complete description below.

SUMMARY OF THE INVENTION

A medical applicator is provided in one embodiment, formed from a pouch or envelope containing a medicinal fluid. The fluid may be, for example, an aqueous antiseptic liquid. An aperture or series of apertures sized to provide proper flow of the viscosity controlled fluid is positioned along the outer surface, along one side of the envelope and a removable, planar cover is positioned over the aperture(s). Here this aperture, or series of apertures, will sometimes be referred to generally as a fluid egress. To use the applicator it is placed in an arrangement for adjusting the temperature of enclosed fluids, for example, in a microwave oven for an appropriate length of time (typically approximately one minute) where the medicinal fluid to be heated (or in a refrigerator or freezer if the medicinal fluid is to be cooled or frozen). The envelope is then removed from the charging device (oven or cooler), the cover peeled from the envelope, and the envelope is then placed with the aperture(s) against the skin of the patient so the warm (or cold) liquid can drain onto the patient's skin. As a result of the heated (or cooled) heat sink fluid, the skin is also simultaneously warmed (or cooled) in a desired manner, sometimes with enhancement of the medicinal effects. The fluid may include a conventional inert viscosity controller to insure proper drainage through the aperture(s) at the selected temperature of the antiseptic liquid.

In another embodiment of the invention a pair of united envelopes having one common wall are presented; the first, a typically larger, carrier envelope contains a heat sink fluid for thermal therapy while the contents of the second envelope provide a medicinal fluid. The fluid in the carrier envelope is for heat storage or cooling purposes and typically remains in the carrier envelope during use, while the second envelope, which is attached in thermoconductive relation to the first, contains a medicinal fluid. The medicinal fluid may be, for example, a sunburn cream, antibiotic solution, ache treatment, lotion or otherwise. The second envelope defines an aperture or series of apertures to provide egress for the medicinal fluid contained therein. A removable cover is provided for selected egress of fluid. In use, the application device can be heated (or cooled) as needed for an appropriate time. Thereafter, it is removed from the source of heating or cooling and is placed against the skin, after the cover is removed, to allow the medicinal liquid to flow through the aperture(s) onto the skin of the patient. Fluids having conventional transdermal properties may be contained in the medicinal fluid-containing envelope of either embodiment if desired, instead of a topical-type fluid.

Both embodiments of the invention as set forth may be designed for refrigeration, heating, or both, for particular soothing vascular constriction and/or other therapeutic purposes depending on the particular application and medications utilized.

DESCRIPTION OF THE PREFERRED EMBODIMENTS

A preferred form of the medical applicator of the invention, at least for certain applications, is shown in FIG.

1. A typical embodiment, according to this version of the invention, will comprise a thin, flexible polymeric pouch or envelope formed from a single, four-mil ply polyethylene. A medicinal liquid is contained within the envelope and comprises an antiseptic solution. While a variety of sizes may be used, in a typical embodiment the envelope may have an overall length of 13 cm and a width of 7 cm. The thickness of the envelope of one particular useful embodiment is one and one half centimeters and it contains 150–250 milliliters of fluid. A series of apertures each having a diameter of approximately one millimeter are defined in the upper surface of the envelope and are surrounded by an adhesive which retains a planar cover thereto.

The preferred method of using the applicator comprises placing the applicator in a temperature-varying appliance, for example, a heating device, at the proper setting to selectively and desirably increase the temperature of the antiseptic fluid contained therein. Thereafter, the envelope is removed, the cover peeled away, and the envelope placed with the apertures against the skin of a patient for warming purposes and so the warm antiseptic fluid can flow from the envelope onto the patient. The envelope can be manually held against the patient's skin or can be affixed as a bandage with adhesive tape, with an elastic sock or bandage, a hook and loop fastener strap or by other means.

DETAILED DESCRIPTION OF THE DRAWINGS AND OPERATION OF THE INVENTION

Figures 1, 2:
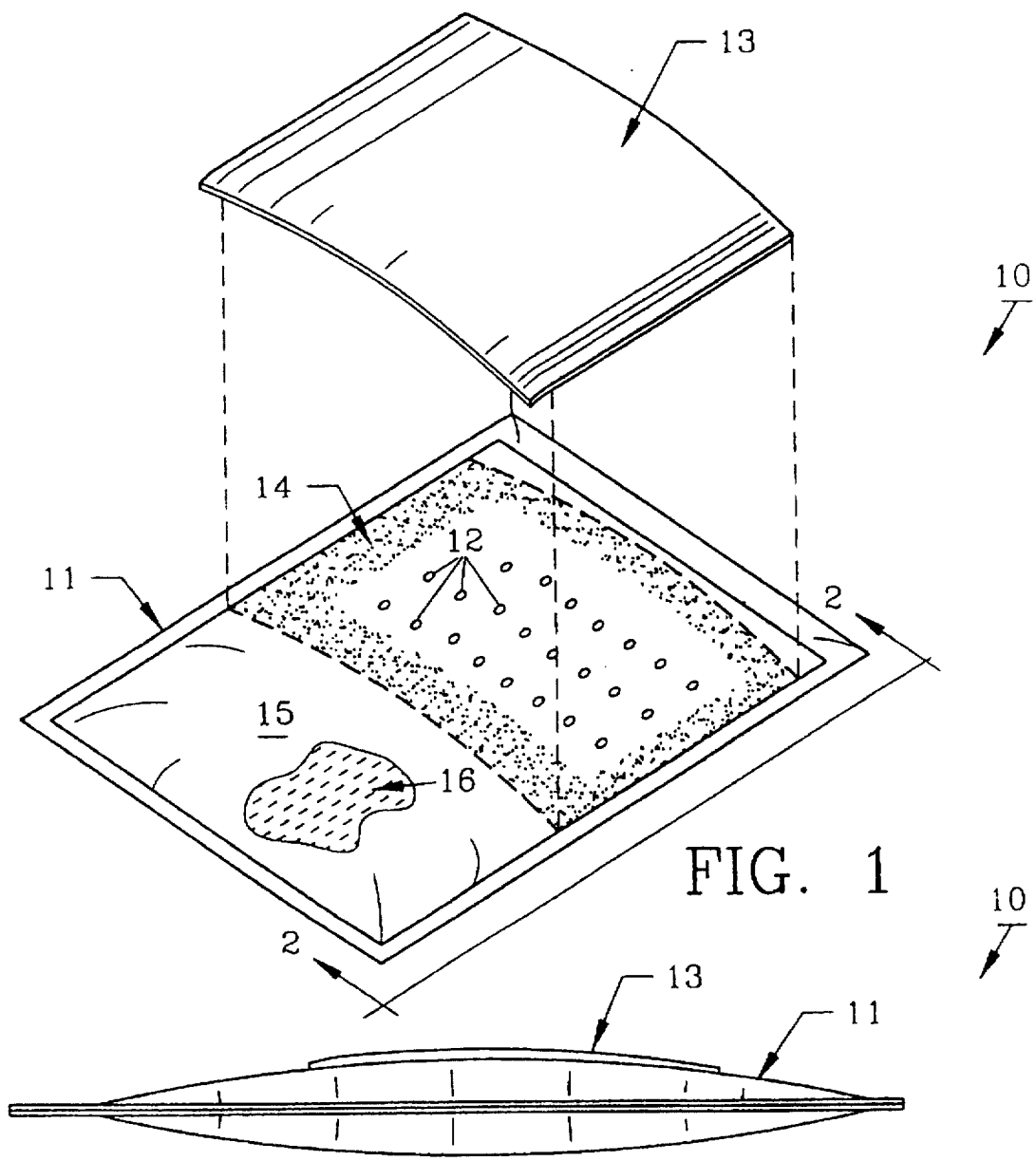
FIG. 1 illustrates a perspective view of the preferred embodiment of the medical applicator with a cover depicted exploded.
FIG. 2 shows the embodiment as seen in FIG. 1 in a side elevational view along lines 2—2 of FIG. 1.

For a more complete understanding of the invention and its operation, turning now to the drawings, FIG. 1 illustrates a preferred form of the invention. Referring to FIG. 1, medical applicator 10 comprises envelope 11 having an egress comprising pattern of apertures 12 exposed as cover 13 has been removed. Envelope 11 may be made from a variety of flexible materials such as polyethylene, nylon reinforced polyethylene, polypropylene, polyvinyl chloride or other polymeric films and materials. Polyethylene has been chosen as the preferred envelope material since it is inert to a wide variety of medical solutions and is relatively inexpensive and readily available. The preferred cover arrangement on cover 13 is likewise formed from polyethylene, preferably as a flat sheet, and is used to block apertures 12 when envelope 11 is not in use. Adhesive 14 surrounds apertures 12 and is preferably a conventional releasable type which allows cover 13 to be peeled from top surface 15 of envelope 11 as desired. As an alternative, cover 13 can be attached to envelope 11 by means of a releasable heat seal such as is standard in packaging and plastics sealing. Envelope 11 contains a medicinal fluid such as an antiseptic liquid, suntan lotion or cream or other fluids which would benefit patients in either a topical or transdermal treatment. The exact medicinal fluid utilized would be dependent on the patient's needs and treatment regimen. For example, it may be aqueous based, but such is not required. It may be an antiseptic, an antibiotic, an analgesic, etc. It may be for topical or transdermal application.

In use, in one example, applicator 10 is placed in a standard microwave oven and irradiated for 1–2 minutes to selectively raise the temperature of fluid 16 therein. Next, applicator 10 is removed from the oven, cover 13 is removed and apertures 12 are directed against the patient's skin to allow medicinal fluid 16 to drain through apertures 12. Envelope 11 can be manually held against the patient's skin. Alternatively, or in addition, adhesives, hook and loop attachments (Velcro® straps), or other holding means may be employed to secure envelope 11 against the patient.

In another application, envelope 11 can be placed in a freezer or refrigerator to allow medicinal fluid 16 contained therein to cool or freeze. Once the temperature of fluid 16 has reached a desired level, the applicator can be removed from the freezer (or refrigerator), cover 13 removed and envelope 11 placed against the patient's skin or against an intermediate layer such as a bandage to cool the skin and to allow fluid 16 to drain through apertures 12 to the desired location thereon. In FIG. 2 envelope 11 is shown with cover 13 adhered by adhesive 14.

Figure 3:
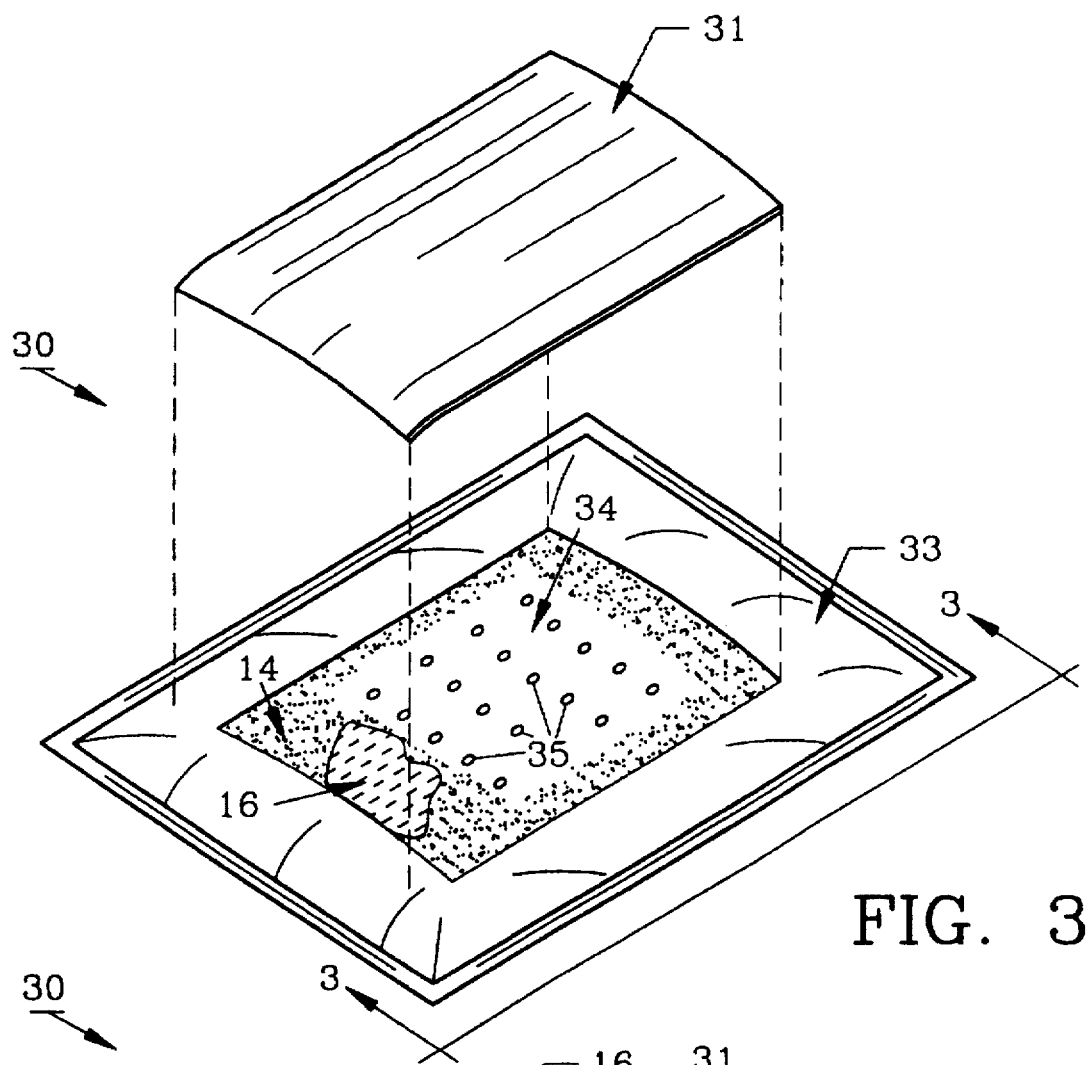
FIG. 3 demonstrates a perspective view of a second embodiment of the invention, with a cover depicted exploded.
Figure 4:
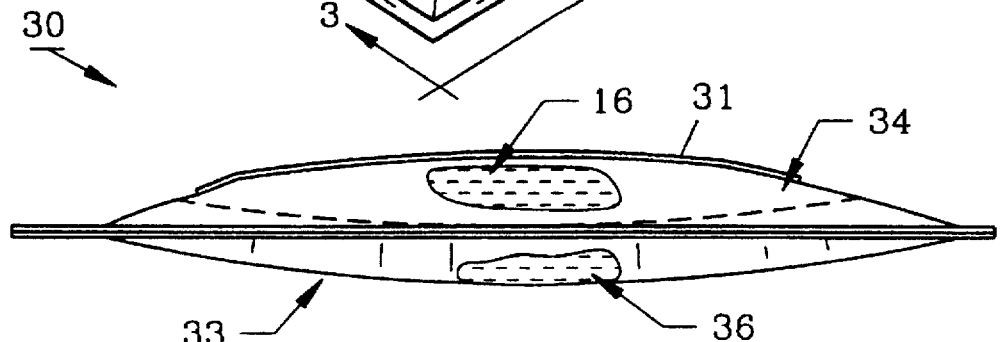
FIG. 4 depicts a side elevational view of the embodiment as seen in FIG. 3 along lines 3—3, with portions broken away to show internal detail.

Another embodiment of the invention is seen in FIGS. 3 and 4 where medical applicator 30 is shown with planar cover 31 removed. Applicator 30 includes a main or carrier envelope 33 and a smaller, medicinal fluid containing envelope 34 attached thereto. Envelope 34 is attached to envelope 33 such as by heat sealing, adhesive, medical fastener or by some other arrangement. Envelope 33 as shown in FIG. 4 is likewise filled with a fluid and may contain, for example, an aqueous liquid, powder, gel or emulsion 36 which could be any of a variety of heat absorbing (storage) substances for either heating or refrigeration purposes as conventionally used. As understood, envelopes 34 and 33 are separate to prevent fluid communication therebetween. As hereinbefore described, envelope 33 has adhesive 14 surrounding apertures 35 which allow medicinal fluid 16 to drain therefrom when used. Envelope 33 acts as a carrier for envelope 34 and could be used when fluid 16 in envelope 34 requires a long period of temperature control or maintenance. Carrier envelope 33 may include a sponge or other liquid absorber and may be maintained under pressure as is common with commercially available therapeutic devices. In use, applicator 30 can be placed in a microwave oven and heated or can be placed into a refrigerator for cooling. Once the ambient temperature of the contents of envelopes 33 and 34 are sufficiently increased or decreased as required, cover 31 is peeled back to expose apertures 35. Thereafter, applicator 30 is placed against the patient's skin and fluid 16 drains through apertures 35 to the selected location on the patient.

Medical applicator 30 of FIGS. 3 and 4 includes a main envelope 33 with a window 37 having secured therein and exposed therethrough a medicinal fluid containing delivery envelope 34, such that the main envelope 33 is in thermal transfer or thermoconductive contact with at least a portion of envelope 34; and envelope 34 is oriented with at least a portion of one surface thereof, having a fluid delivery egress therein exposed and oriented for delivery of fluid contained within envelope 34. Prior to use to deliver fluid, this exposed portion of the surface of envelope 34 is covered by cover 31. In general, the operation of the assembly of FIGS. 3 and 4 is that the material contained with the main envelope 33 is a thermal storage material, which will remain either heated or cooled for a substantial period of time, depending on the use. This will have the effect of maintaining the fluid within envelope 34 either heated or cooled for a substantial period of time. Further, it can be used to apply the heat or cooling to the surface of the patient, to which medicinal fluid is transferred from envelope 34.

It will be generally preferred to retain carrier envelope 33 in association with delivery envelope 34, such that a substantial portion of surface overlap therebetween is provided for heat sealing, adhesive attachment or otherwise. In an alternative arrangement not shown, envelope 34 may be inside of a closed envelope without a window, and attached thereto such that one surface thereof is in contact with a surface of envelope 33. Of course, in such an arrangement the egress apertures would project through both envelopes.

Figure 5:
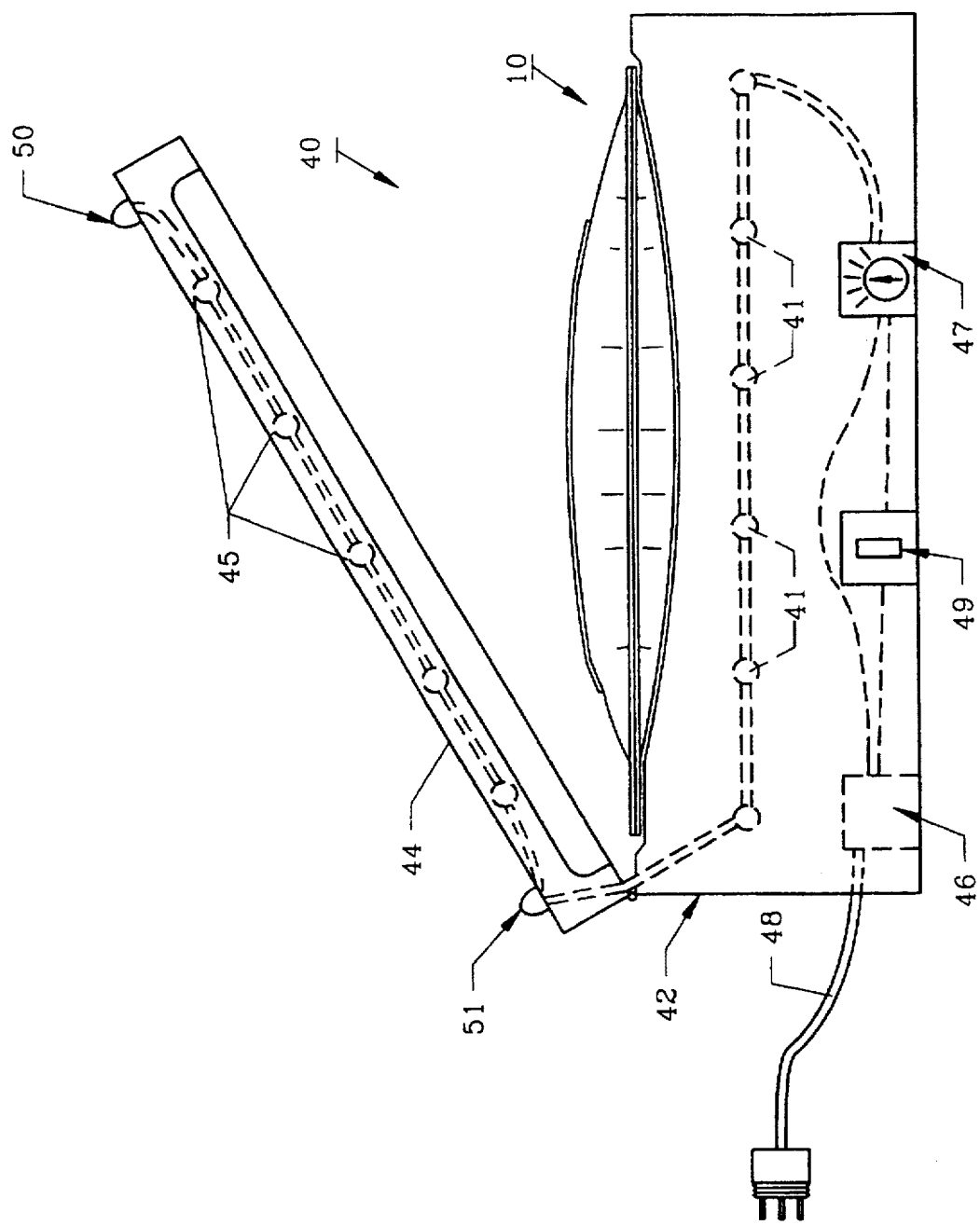
FIG. 5 features a resistance heating device for use in the method as described.

Heating device 40 is shown in FIG. 5. As seen, heating device 40 is of the electrical resistance type having heating elements contained within cabinet 42. Cabinet 42 includes shelf 43 for placement of medical applicator 10 thereon. Lid 44 likewise includes a series of heating elements 45 whereby applicator 10 can be heated quickly to the desired temperature in approximately 1-2 minutes. In use, ON/OFF switch 46 is turned on and thermostat 47 adjusted. AC current flows through supply cord 48 to circuitry 49 which is regulated by thermostat 47. Medical applicator 10 is placed on shelf 43, lid 44 closed and applicator 10 heated in about 1-2 minutes. Red LED 51 demonstrates, when activated, that power is connected to heating device 10 and green activated LED 50 signals that heating is complete. Once heated, applicator 10 is removed and used as hereinbefore described.

The illustrations and examples herein are for explanatory purposes as other devices than those described are available for heating the medical applicator, and another embodiment of the applicator may include reactive chemicals to provide the desired heat, such as iron oxide compounds which will quickly react exothermically for a heat source. Also, numerous general applications of materials and techniques according to the present invention will be apparent. For example, the egress or aperture arrangement in the envelope for delivery of medicinal fluid, may comprise a single aperture or plurality of apertures and may comprise apertures in various shapes, sizes or patterns, for a preferred or most desired delivery of the medicinal fluid. The medicinal fluid may be of a wide variety of types and content. It may be developed specifically for topical application or administration of therapeutic material, or transdermal delivery, or both. Herein the term "medicinal fluid" is not meant to be limiting in any manner, other than to refer to a flowable substance which could be transferred from inside an envelope, through an aperture arrangement, to an exterior thereof, for selected therapeutic purposes. Such medicinal fluid may include adjuvants such as carriers, dyes, fragrances, etc., in addition to therapeutic agent(s). The device may be developed and utilized specifically for treatment of humans, or for veterinary medical applications.

The material from which the arrangement is constructed may be of a wide variety of types. Flexible materials that will be convenient to handle and apply, will be preferred. Films of the type described above will typically be most preferred since they are relatively inexpensive and various arrangements according to the present invention will be developed for disposal after use.

When the embodiment of FIGS. 3 and 4 is practiced, the thermal storage material included within the larger remaining envelope may be of a wide variety of types, depending on the specific application. Usually a material which will retain heat (or cold) for a substantial period of time, will be preferred as will a material which possesses water or paraffin emulsions. Some examples of such materials include thermal fluids and hydrostatic gels.

A wide variety of heating or cooling sources may be utilized to prepare arrangements according to the present invention for preferred use. These may even include ambient conditions. Materials from which the applicators according to the present invention are constructed may be selected to readily absorb solar energy, for field use. Such materials will at least in part be dependent upon the particular means for heating or cooling the applicator. For example, if microwave heating systems are to be used, then the material chosen is a material which is transparent to microwave energy. As indicated previously, if solar heating is to be used, a material which readily absorbs solar energy would be preferred.

Any of a wide variety of adhesives may be utilized at seams or seals in the arrangement, as long as the adhesives do not interfere with the operation and they maintain the appropriate level of sealing needed.

In some commercial applications the applicator may be stored within an exterior tear-away package, until used. Such packaging may be selected, for example, to provide for a sterile or antiseptic environment.

Such applications and embodiments are not intended to limit the scope of the appended claims.

We claim:

1. A method of controlling body tissue temperature during administration of medication, said method comprising steps of:
   (a) providing a medical applicator comprising a medicinal fluid containing envelope and a carrier envelope,
      (i) said medicinal fluid containing envelope including a fluid egress surface and a peel away cover provided over the fluid egress surface, and having a medicinal fluid provided within the medicinal fluid containing envelope for medical treatment of body tissue,
      (ii) said carrier envelope including a thermal storage material enclosed therein for thermal treatment of body tissue;
   (b) heating the thermal storage material in the carrier envelope to a desired temperature for thermal treatment of body tissue,
   (c) combining the medicinal fluid containing envelope and the carrier envelope;
   (d) peeling the cover to expose the fluid egress surface and applying the exposed fluid egress surface to a portion of body tissue;
   (e) releasing medicinal fluid from the medicinal fluid containing envelope through the fluid egress surface to provide application of medicinal fluid to the portion of body tissue;
   (f) controlling the duration of medicinal fluid application.

2. A method of controlling tissue temperature during administration of medication according to claim 1, wherein the step of heating the thermal storage material includes heating by a microwave heating system.

3. A method of controlling tissue temperature during administration of medication according to claim 2, wherein the step of heating occurs for between one to two minutes.

4. A method of controlling tissue temperature during administration of medication according to claim 1, wherein the step of heating the thermal storage material includes heating by placement within an electrical resistance heating device.

5. A method of controlling tissue temperature during administration of medication according to claim 1, wherein the medicinal fluid includes a therapeutic agent and a carrier.

6. A method of controlling tissue temperature during administration of medication according to claims 1, wherein said steps releasing medicinal fluid and controlling body tissue temperature occur simultaneously.

7. A method of controlling tissue temperature during administration of medication according to claim 1, further comprising a step of storing the medical applicator in a sterile environment.

8. A method of controlling tissue temperature during administration of medication according to claim 1, further comprising a step of storing the medical applicator in an antiseptic environment.

9. A method of controlling tissue temperature during administration of medication according to claim 1, further comprising storing the medical applicator in an exterior tear-away package.

10. A method of controlling tissue temperature during administration of medication according to claim 1, wherein the thermal storage material comprises a paraffin emulsion.

11. A method of controlling tissue temperature during administration of medication according to claim 1, wherein the fluid egress surface comprises a pattern of apertures.

* * * * *

UNITED STATES PATENT AND TRADEMARK OFFICE
CERTIFICATE OF CORRECTION

PATENT NO. : 5,730,721

DATED : MARCH 24, 1998

INVENTOR(S) : HYATT ET AL.

It is certified that error appears in the above-identified patent and that said Letters Patent is hereby corrected as shown below:

Title page, [56] References Cited, U.S. Patent Documents: insert the following references in appropriate numerical order: —4,127,339 11/1978 Malacheski et al.; 4,177,811 12/1979 Alvarez; 4,419,568 12/1983 Van Overloop; 4,495,402 1/1985 Burdick et al.; 4,963,360 10/1990 Argaud; 5,380,110 1/1995 Festa—

Front page, [56] References Cited, Foreign Patent Documents: insert —DE 3441594 5/1986 Germany; GB 2,205,496 12/1988 Great Britain; EP 0 360 270 3/1990 Europe; WO 93/07842 4/1993 PCT, WO85/02124 5/1985 PCT—.

Col. 4, line 65: insert —41— after "elements"

Signed and Sealed this

Ninth Day of May, 2000

Attest:

Attesting Officer

Q. TODD DICKINSON

Director of Patents and Trademarks